United States Patent [19]

Davis

[11] Patent Number: 5,410,157
[45] Date of Patent: Apr. 25, 1995

[54] BOOK DIMENSION DETECTOR

[75] Inventor: Lawrence R. Davis, Torrance, Calif.

[73] Assignee: R.R. Donnelley & Sons Company, Lisle, Ill.

[21] Appl. No.: 254,473

[22] Filed: Jun. 6, 1994

Related U.S. Application Data

[63] Continuation of Ser. No. 906,550, Jun. 30, 1992, abandoned.

[51] Int. Cl.⁶ .......................................... G01N 21/86
[52] U.S. Cl. ...................................... 250/560; 356/383
[58] Field of Search ..................... 250/560, 221, 222.1, 250/223 R; 356/383, 384, 385, 386, 387; 83/80; 209/577, 579, 586

[56] References Cited

U.S. PATENT DOCUMENTS

| | | | |
|---|---|---|---|
| 3,292,469 | 12/1966 | Vaccaro | 83/80 |
| 3,461,759 | 8/1969 | Dixon et al. | 83/80 |
| 3,682,554 | 8/1972 | Flacynski | 250/223 R |
| 3,736,063 | 5/1973 | Ohno et al. | 356/385 |
| 3,804,404 | 4/1974 | Bosshard | 271/57 |
| 4,170,306 | 10/1979 | Marshall et al. | 356/407 |
| 4,187,545 | 2/1980 | Wallace et al. | 356/386 |
| 4,245,243 | 1/1981 | Gutjahr et al. | 250/223 R |
| 4,461,576 | 7/1984 | King | 250/560 |
| 4,541,317 | 9/1985 | Van Humbeeck et al. | 83/34 |
| 5,007,739 | 4/1991 | Shimano et al. | 250/560 |
| 5,142,158 | 8/1992 | Craig, Jr. | 250/560 |
| 5,202,557 | 4/1993 | Robertson | 250/560 |

Primary Examiner—David C. Nelms
Attorney, Agent, or Firm—Marshall, O'Toole, Gerstein, Murray & Borun

[57] ABSTRACT

The present invention detects a bad book, i.e. one having improper dimensions, by relying upon sensors for sensing the leading and trailing edges of the book and upon a circuit responsive to the sensors for detecting a bad book. A blocked sensor detector is provided for determining if one or more sensors are improperly blocked.

27 Claims, 3 Drawing Sheets

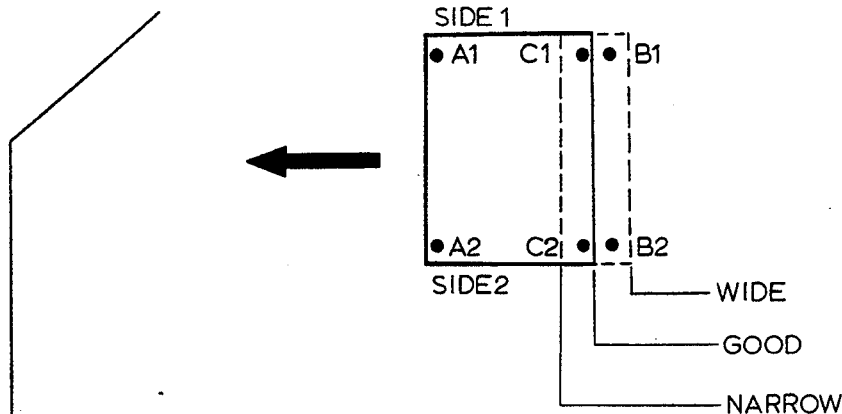
FIG 2
| A1 | B1 | C1 | SIDE 1 |
|---|---|---|---|
| 1 | 0 | 0 | WIDE 0 |
| 1 | 0 | 1 | IMPOSSIBLE 0 |
| 1 | 1 | 0 | GOOD 1 |
| 1 | 1 | 1 | NARROW 0 |
| A2 | B2 | C2 | SIDE 2 |
|---|---|---|---|
| 1 | 0 | 0 | WIDE 0 |
| 1 | 0 | 1 | IMPOSSIBLE 0 |
| 1 | 1 | 0 | GOOD 1 |
| 1 | 1 | 1 | NARROW 0 |
| SIDE 1 | SIDE 2 | BOOK |
|---|---|---|
| 0 | 0 | BAD 0 |
| 0 | 1 | BAD 0 |
| 1 | 0 | BAD 0 |
| 1 | 1 | GOOD 1 |
FIG. 4
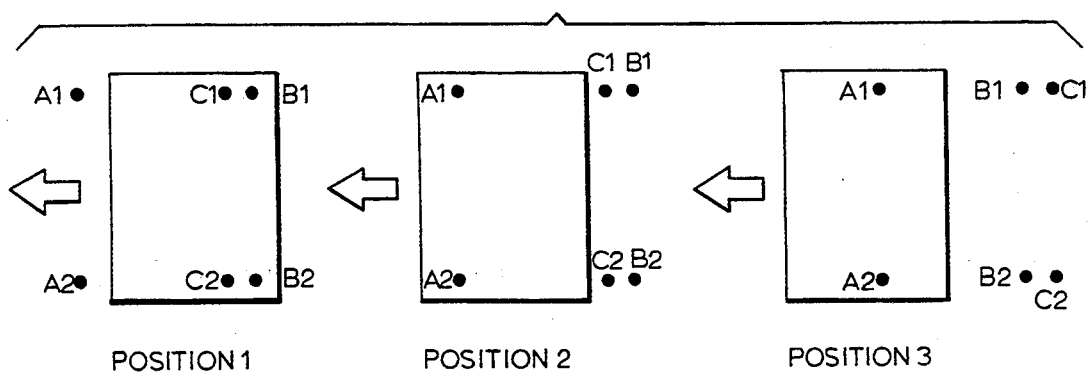
POSITION 1   POSITION 2   POSITION 3

BOOK DIMENSION DETECTOR

This is a continuation of U.S. application Ser No. 07/906,550, filed June 30, 1992, now abandoned.

The present invention relates to the detection of the dimensions of books and, more particularly, to the detection of books having improper dimensions.

BACKGROUND OF THE INVENTION

Books travelling down a conveyor system of a binding line can have a variety of defects which reduce the quality of the finished product. For example, the trimmer that trims off excess paper from the books (including magazines or the like), may cut the top edge, bottom edge, the leading edge and/or the trailing edge of the books short, long or at an angle resulting in the books having improper dimensions or appearing crooked. In severe cases, portions of images and/or text may be cut from the book. Such books are difficult to stack and to bind for shipping and are likely to be rejected by the customer.

Books having improper dimensions must be detected promptly so that waste can be minimized by correcting the faulty condition, such as improper operation of the trimmer or other equipment on the binding line, which is causing the books to have the improper dimensions.

SUMMARY OF THE INVENTION

The present invention detects improper dimensions of a book by employing sensors for sensing the edges of the book and a circuit responsive to the sensors for detecting the improper dimensions.

According to one aspect of the invention, a first sensor senses a first edge of the book and second and third sensors sense a second edge of the book. The first, second and third sensors are spaced so that a good book (i.e. one having the proper dimensions) covers the first and third sensors but not the second sensor. The circuit is connected to the first, second and third sensors and is responsive to the first sensor in order to provide a good book output when the first and third sensors but not the second sensor are covered by the book and to provide a bad book output otherwise.

According to another aspect of the invention, a first sensor senses a leading edge of the book at its top and second and third sensors sense a trailing edge of the book at its top. Additionally, a fourth sensor senses the leading edge of the book at its bottom, and fifth and sixth sensors sense the trailing edge of the book at its bottom. A circuit is connected to the first, second, and third sensors and is responsive to the first sensor to provide a top good book output when the first and third sensors, but not the second sensor, are covered by the book and to provide a top bad book output otherwise. Similarly, the circuit is connected to the fourth, fifth, and sixth sensors and is responsive to the fourth sensor to provide a bottom good book output when the fourth and sixth sensors, but not the fifth sensor, are covered by the book and to provide a bottom bad book output otherwise. In this way, by properly locating the sensors, the system can insure that the book is square and of the proper dimensions.

According to yet another aspect of the invention, a blocked sensor detector is responsive to the sensors in order to determine if the sensors are experiencing a blocked sensor failure mode in which the sensors are improperly indicating a blocked condition. That is, the blocked sensor detector samples the sensors during sample periods, i.e. when they are unblocked by the book, and provides an appropriate output if any of the sensors indicate a blocked state during these sampling periods.

BRIEF DESCRIPTION OF THE DRAWINGS

These and other features and advantages will become more apparent from a detailed consideration of the invention when taken in conjunction with the drawings in which:

FIGS. 1 and 1A illustrate the invention in conjunction with a book conveyor line including a trimmer;

FIG. 2 illustrates truth tables useful in explaining the invention;

DETAILED DESCRIPTION

Figure 1:
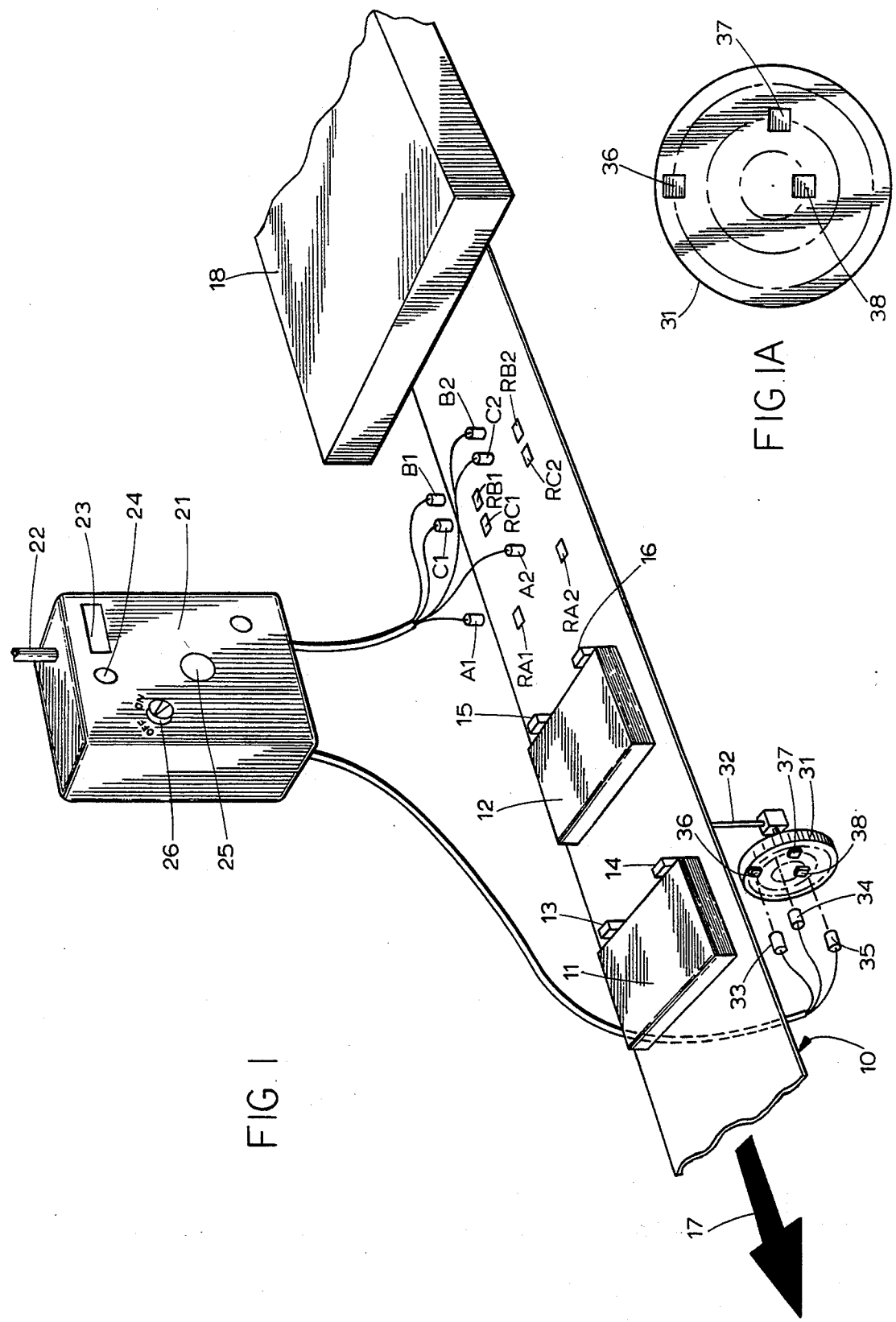
Figure 3:
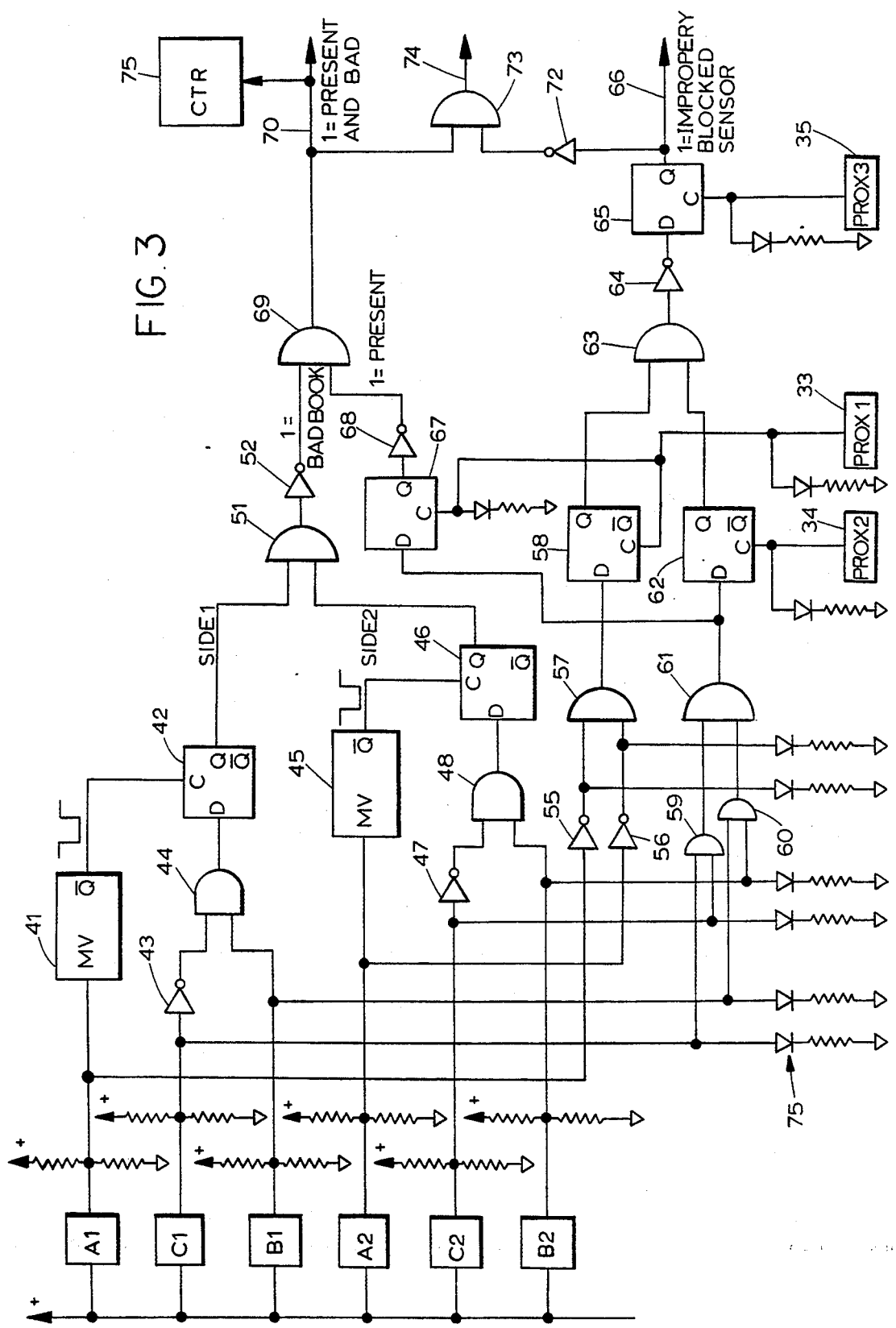
FIG. 3 is an electronic circuit used in conjunction with the sensors shown in FIG. 1 for implementing the truth tables shown in FIG. 2; and, FIG. 4 shows the sampling periods during which the sensors are sampled to determine if the sensors are functioning properly.

As shown in FIG. 1, a conveyor 10 transports books 11 and 12 by means of conveyor lugs 13,14 and 15,16, respectively, in the direction of the arrow 17. The books may comprise magazines, catalogs or the like. Six sensors A1, B1, C1, A2, B2, and C2 are positioned according to the proper size of the books exiting a trimmer 18. The trimmer 18 trims off excess paper from the books as the books travel down the binding line. The sensors A1–C1 and A2–C2 may be F52-65 fiber optic light detecting eyes manufactured by Keyence. The operation of these sensors may be selected by operation of a switch on the sensor to provide a high state output (i.e. a "1") or a low state output (i.e. a "0") in the presence of light. In the present invention, the sensors A1 and A2 are arranged to provide a "1" output in the absence of light (i.e. dark on) whereas the detectors B1, B2, C1, and C2 are arranged to provide a "1" output in the presence of light (i.e. light on). Any other combination of light on/dark on sensors may be used for the sensors A1–C1 and A2–C2 provided the logic shown in FIG. 3 is appropriately modified.

These sensors A1–C2 are capable of operating in either a reflective mode, wherein they emit light and sense the presence or absence of a reflection of the emitted light, or an external light mode, wherein they sense the presence or absence of light from an external light source. In the preferred embodiment, the sensors A1–C2 are operated in the reflective mode. Accordingly, reflective tape segments RA1, RA2, RB1, RB2, RC1 and RC2 are adhesively attached to the conveyor 10 at positions corresponding to the positions of the sensors A1–C2. The sensors A1–C2 are then positioned close enough to their corresponding segments of reflective tape so that they can detect whether or not the light paths between the sensors A1–C2 and their corresponding segments of reflective tape are blocked by a book when the dimensions of the book are to be detected, but far enough away to provide clearance for the books 11 and 12. A blocked light path between a sensor and its corresponding reflective tape segment may be referred to herein simply as a blocked sensor.

Alternatively, if the conveyor is a chain-type conveyor, the sensors A1–C2 may be operated in the external light source mode. If so, one or more light sources may be located beneath the conveyor to shine light up through the gaps between the links of the conveyor and toward the sensors A1–C1 and A2–C2.

The sensors A1–C1 and A2–C2 are connected by fiber optic cables to a box 21 which receives power from AC lines 22. The box 21 contains the electronics shown in FIG. 3 and may also contain a counter 23 for counting books having improper dimensions, a counter reset button 24, a bad book indicating light 25, and a control switch 26 for turning the system on. Although not shown, the box 21 may also contain, if desired, a reject relay which can be operated when a book having improper dimensions is detected. The reject relay can operate a diverting means in the conveyor system to divert those books having improper dimensions to a reject bin.

The system shown in FIG. 1 also contains a disc 31 suitably driven by a shaft and gear set 32 in synchronism with the conveyor 10. The disc 31 operates in association with proximity sensors 33, 34 and 35 (which may be in the form of Hall Effect devices) to indicate sampling periods during which a book is in selected positions as it is transported along the conveyor line 10. These positions are shown in FIG. 4 and define the sampling periods for determining whether any of the sensors A1, A2, B1, B2, C1 and C2 are experiencing a blocked sensor failure mode. Such a sensor provides an output indicating that the sensor is blocked by a book when it in fact is not so blocked. FIG. 1A shows suitable devices 36, 37 and 38 (such as magnets) mounted on the face of the disc 31. The proximity of these devices 36, 37 and 38 is sensed by a corresponding proximity sensor 33, 34 and 35 to provide appropriate signals at the corresponding positions shown in FIG. 4. Thus, proximity sensor 33 provides a PROX 1 signal for position 1, proximity sensor 34 provides a PROX 2 signal for position 2, and proximity sensor 35 provides a PROX 3 signal for position 3. The disc 31 may instead be a cam driven in synchronism with the conveyor 10, and the proximity sensors 33–35 may instead be limit switches operated by the cam at the specified FIG. 4 positions of the books as they move down the conveyor.

As indicated above, the sensors A1–C2 and the segments RA1–RC2 of reflective tape are position adjusted according to the proper dimensions of the books exiting the trimmer 17. Shown in FIG. 2 is a book in relation to the six edge sensors A1–C1 and A2–C2, it being understood that the positions of the reflective tape segments RA1–RC2 on the conveyor 10 are substantially the same as their corresponding sensors A1–C2 above the conveyor 10. Sensors A1 and A2 sense the leading edge of a book (i.e. the front edge of the book as the book is transported along the conveyor) and sensors B1, B2, C1, and C2 sense the trailing edge of a book (i.e. the back edge of the book as the book is transported along the conveyor). The sensors A1–C1 and the sensors A2–C2 are positioned with respect to a book to sense whether books are wide, good or narrow. That is, a book which is narrow at its top (i.e. side 1 of the book) cannot cover the sensor C1 at the same time that it covers the sensor A1, and a book which is narrow at its bottom (i.e. side 2) cannot cover the sensor C2 at the same time that it covers the sensor A2. Furthermore, a book which is wide at its top covers both of the sensors B1 and C1 at the same time that it covers the sensor A1, and a book which is wide at its bottom covers both of the sensors B2 and C2 at the same time that it covers the sensor A2. The positions of sensors B1 and C1 are adjusted, with respect to one another, depending upon the allowable tolerance range for the width of a good book at its top. Similarly, the positions of sensors B2 and C2 are adjusted, with respect to one another, depending upon the allowable tolerance range for the width of a good book at its bottom. The segments RB1, RB2, RC1 and RC2 must be similarly adjusted.

Also shown in FIG. 2 are the truth tables which logically describe the combinations of sensor outputs from the sensors A1, B1, C1, A2, B2, and C2 indicating whether a book is wide, good or narrow. The outputs of sensors B1, B2, C1, and C2 are sampled when sensors A1 and A2 sense the leading edge of a book (i.e. when sensors A1 and A2 are just blocked by a book). Since the outputs of the sensors B1, B2, C1, and C2 are irrelevant to the determination of whether the book has proper dimensions until the outputs from the sensors A1 and A2 are "1" (indicating that the sensors A1 and A2 are blocked by a book), the truth tables do not show the cases where the outputs from the sensors A1 and A2 are "0".

Therefore, the truth table with respect to side 1 has four rows representing the four combinations of the outputs from the sensors B1 and C1 which sense the width of the top (side 1) of the book when the output from sensor A1 is "1". At the time when the sensor A1 first senses the leading edge of the book, i.e. the sensor A1 is blocked by the book so that it provides a "1" output, (a) a wide book blocks both the sensor B1 and the sensor C1 so that the sensors B1 and C1 each provides a "0" output, (b) a good book blocks the sensor C1 but not the sensor B1 so that the output of the sensor C1 is a "0" and the output of the sensor B1 is a "1", and (c) a narrow book blocks neither of the sensors B1 and C1 so that the sensors B1 and C1 each provides a "1" output. Blocking of the sensors A1 and B1 but not the sensor C1 is an impossible condition and is ignored.

Similarly, the truth table with respect to side 2 has four rows representing the four combinations of the outputs from the sensors B2 and C2 which sense the width at the bottom (side 2) of the book when the output from sensor A2 is "1". As can be seen from this truth table, the outputs of the sensors A2, B2, and C2 indicate proper or improper width at the bottom of the book in the same way that the outputs of the sensors A1, B1, and C1 indicate proper or improper width at the top of the book.

The third truth table shown in FIG. 2 combines the side 1 and side 2 logic shown in the first two truth tables to determine whether both the top and the bottom the book are properly dimensioned so that the book is a good book. Thus, if the side 1 logic provides a "1" output and the side 2 logic provides a "1" output, the book is good. Otherwise, the book is bad.

FIG. 3 illustrates an electronic circuit for implementing the truth tables shown in FIG. 2 and also for implementing the detection of a malfunctioning edge sensor logic. The sensor A1 is connected to the input of a monostable multivibrator 41 having a Q output which is connected to the clock terminal (C) of a D flip-flop 42. The sensor C1 is connected through an inverter 43 to one input of an AND gate 44. The sensor B1 is connected to the other input of the AND gate 44. The output of the AND gate 44 is connected to the D terminal of the D flip-flop 42 having a Q output terminal which provides the side 1 output.

Similarly, the sensor A2 is connected to the input of a monostable multivibrator 45 having a Q output which is connected to the clock terminal of a D flip-flop 46.

The sensor C2 is connected through an inverter 47 to one input of an AND gate 48. The sensor B2 is connected to the other input of the AND gate 48. The output of the AND gate 48 is connected to the D terminal of the D flip-flop 46 having a Q output terminal which provides the side 2 output.

When the inputs to the multivibrators 41 and 45 are supplied with a "1" (because their associated edge sensors A1 and A2 are just blocked by the leading edge of a book), the Q outputs of these monostable multivibrators 41 and 45 provide negative going pulses which may, for example, be 25 microseconds in duration. The trailing edge of this pulse, i.e. the positive going edge, causes the corresponding D flip-flops 42 and 46 to clock through the inputs at their respective D input terminals to their respective Q output terminals. The 25 microsecond delay provided by the monostable multivibrators 41 and 45 compensates for any delays in the responses from the sensors A1–C1 and A2–C2 and for any propagation delays of the circuit.

When the D flip-flops 42 and 46 receive clocking pulses from their respective monostable multivibrators 41 and 45, the D flip-flops 42 and 46 sample the outputs from the sensors B1, B2, C1, and C2. A properly dimensioned book blocks the sensors C1 and C2 but not the sensors B1 and B2 at the time that these sensors are sampled and, as a result, the outputs of the sensors C1 and C2 are at a "0" logic level and the outputs of the sensors B1 and B2 are at a "1" logic level. The "0" outputs from the sensors C1 and C2 are inverted by the corresponding inverters 43 and 47 to supply a "1" to one input of the AND gates 44 and 48, respectively. The "1" outputs from the sensors B1 and B2 are supplied directly to other inputs of the AND gates 44 and 48, respectively. Under these conditions, therefore, both of the AND gates 44 and 48 provide a "1" input to the D terminals of the corresponding D flip-flops 42 and 46. The trailing edge of the clock pulses supplied by the respective monostable multivibrators 41 and 45 cause the "1" inputs at the D terminal of the flip-flops 42 and 46 to be clocked through to their respective Q output terminals. Thus, for each "good" book, the clock terminals of the D flip-flops 42 and 46 continue to be clocked when the sensors C1 and C2 are blocked and the sensors B1 and B2 are not blocked so that the Q outputs of the D flip-flop 42 and 46 remain at a "1" logic level. An AND gate 51 receives these "1" outputs from the D flip-flops 42 and 46. With both inputs at a logic level "1", the AND gate 51 supplies a "1" output which is inverted by inverter 52 to a "0" indicating that the book is "good".

When the leading edge of a book which is narrow at its top is sensed by the sensor A1, the sensor C1 is not blocked and the output from the sensor C1 is a "1" which is inverted by inverter 43 to a "0". This "0" is provided to the AND gate 44 which, accordingly, provides a "0" to the D input terminal of the D flip-flop 42. When the trailing edge of the pulse from the monostable multivibrator 41 is produced, the D flip-flop 42 clocks the "0" at its D input through to its Q output and provides this "0" to one input of the AND gate 51 causing the AND gate 51 to provide a "0" to the inverter 52. The inverter 52 inverts this "0" to a "1" indicating that the book is "bad". On the other hand, when the leading edge of a book which is wide at its top is sensed by sensor A1, the sensor B1 is blocked and the output from the sensor B1 is a "0". This "0" is provided to the AND gate 44 which, accordingly, provides a "0" to the D input terminal of the D flip-flop 42. When the trailing edge of the pulse from the monostable multivibrator 41 is produced, the D flip-flop 42 clocks the "0" at its D input through to its Q output causing the AND gate 51 to provide a "0" to the inverter 52. The inverter 52 inverts this "0" to a "1" indicating that the book is "bad".

The side 2 circuitry operates in a similar fashion as that described above. Therefore, a "0" output from either or both of the D flip-flops 42 and 46 causes the AND gate 51 to supply a "0" output indicating a "bad" book.

The outputs of the sensors A1 and A2 are also connected through respective inverters 55 and 56 to corresponding inputs of an AND gate 57. The output of the AND gate 57 is connected to the D terminal of a D flip-flop 58. The sensors C1 and C2 are connected to respective inputs of an AND gate 59, and the sensors B1 and B2 are connected to respective inputs of an AND gate 60. The outputs of the AND gates 59 and 60 are connected to respective inputs of an AND gate 61 having an output which is connected to the D terminal of a D flip-flop 62.

The clock terminal of the D flip-flop 58 receives a high signal from the proximity sensor 33 which senses position 1 of a book as shown in FIG. 4. When a book is in position 1, the sensors A1 and A2 are not blocked by a book. Accordingly, if the sensors A1 and A2 are not experiencing a blocked failure mode, they provide "0" outputs. (A sensor which is experiencing a blocked failure mode has failed in a condition indicating that it is blocked when it is not or is permanently blocked by dirt or debris.) These "0" outputs are inverted by the inverters 55 and 56 to provide "1" inputs to the AND gate 57. The output of the AND gate 57 is accordingly a "1" which is provided to the D input of the D flip-flop 58. When a leading edge of a clock pulse is received from the proximity sensor 33, the D flip-flop 58 clocks the "1" at its D input through to its Q output. This "1" at the Q output of the D flip-flop 58 is provided to one input of an AND gate 63. However, if one (or both) of the sensors A1 and A2 experiences a blocked failure mode, a "0" is provided to the D flip-flop 58 by one or both of the inverters 55, 56 and the AND gate 57. When the D flip-flop 58 is clocked by the proximity sensor 33, the D flip-flop 58 clocks this "0" at its D input through to its Q output and, accordingly, to one input of the AND gate 63 causing the output of the AND gate 63 to be at a "0" state. This "0" from the output of the AND gate 63 is inverted by an inverter 64 to a "1" indicating a permanently blocked or malfunctioning sensor.

The clock terminal of the D flip-flop 62 receives a clock pulse from the proximity sensor 34 which senses position 2 as shown in FIG. 4. If one of the sensors B1, C1, B2, or C2 improperly indicates a blocked condition when position 2 is reached, the output of the AND gate 61 is a "0" (instead of the "1" which is the output of the AND gate 61 if all of the sensors B1, B2, C1 and C2 are properly responding to light). The "0" output of the AND gate 61 indicating a blocked sensor failure mode causes the Q output of the D flip-flop 62 to assume a "0" state when a leading edge of a clock pulse is produced by the proximity sensor 34 at the position 2. This "0" causes the output of the AND gate 63 to be "0" and the output of the inverter 64 to be "1" indicating a malfunctioning sensor. Thus, if any of the sensors A1–C1 and A2–C2 indicates that it is blocked when in fact it is not blocked, the output of the inverter 64 is at a "1" logic level. On the other hand, if these sensors are operating properly, the output of the inverter 64 is at a "0" logic level. The output of the inverter 64 is connected to the D terminal of a D flip-flop 65.

When the position 3 is attained, a clock pulse is supplied by the proximity sensor 35 to the clock terminal of the D flip-flop 65. The leading edge of this clock pulse causes the Q output of the D flip-flop 65 to assume the state of its D input terminal. Accordingly, if the D input of the D flip-flop 65 receives a "1" from the output of the inverter 64 (because a sensor is improperly indicating a blocked condition), this "1" input is clocked by the D flip-flop 65 to its output and is supplied to terminal 66 to indicate an improperly functioning sensor. On the other hand, a "0" at the Q output of the D flip-flop 65 indicates that the sensors are functioning properly.

A D flip-flop 67 has a D input connected to the output of the AND gate 61. A clock terminal of the D flip-flop 67 receives a clock pulse from the proximity sensor 33 when the book is in position 1. A Q output of the D flip-flop 67 is connected through an inverter 68 to one input of the AND gate 69. The other input of the AND gate 69 receives the output of the inverter 52. Assuming that the sensors B1, B2, C1, and C2 are not experiencing a blocked failure mode, the D flip-flop 67 indicates that the sensors B1, B2, C1, and C2 have sensed the "presence" of a book at the position 1. As long as any of the sensors B1, B2, C1, and C2 are blocked each time the proximity sensor 33 detects position 1, the D flip-flop 67 will provide a "0" at its Q output. This "0" is inverted by inverter 68 so that a "1" is supplied to the second input of the AND gate 69. (It should be noted that, if any of the sensors B1, B2, C1, or C2 is experiencing a blocked failure mode, the outputs of the AND gate 61 and of the D flip-flop 67 remain at "0" logic levels and the output of the inverter 68 may falsely indicate the "presence" of a book in the position 1 when, in fact, a book is not so present. This condition is, however, indicated by the output of the D flip-flop 65.) Accordingly, if a book is present in position 1, any bad book signal (i.e. a "1" from the inverter 52) is passed through the AND gate 69 to an output terminal 70. On the other hand, if the book is not bad, the inverter 52 supplies a "0" to the first input of the AND gate 69 so that its output is at a logic level "0" indicating that the book is not bad.

The output of the D flip-flop 65 may be connected through an inverter 72 to a first input of an AND gate 73, and the output of the AND gate 69 may be connected to a second input of the AND gate 73. An output terminal 74 of the AND gate 73 is at a "1" logic level if (a) a book is "present", (b) the book is bad, and (c) a blocked sensor failure mode has not been detected. The output terminal 74 of the AND gate 73 is at a "0" logic level if (a) the book is good, or (b) a book is not present, or (c) a blocked sensor failure mode has been detected. As should be evident from an inspection of the Figures, in order for the signal produced by the AND gate 73 to provide an accurate indication of bad books when all sensors are functioning properly, the sensors A1–C2, the reflective tape segments RA1–RC2, the sensors 33–35, and the magnets 36–38 must be positioned to insure that the light paths between the sensors A1–C2 and their corresponding reflective tape segments RA-1–RC2 are either appropriately blocked or appropriately not blocked by a book when it is in the positions 1 and 2. That is, when a book is in position 1, the light paths between the sensors A1 and A2 and their corresponding reflective tape segments RA1 and RA2 should be unblocked so that the Q output of the D flip-flop 58 is a "1", and the light path between at least one of the sensors B1, B2, C1, or C2 and its corresponding reflective tape segment RB1, RB2, RC1, or RC2 should be blocked so that the Q output of the D flip-flop 67 is a "0". Likewise, when a book is in position 2, the light paths between the sensors B1, B2, C1, and C2 and their corresponding reflective tape segments RB1, RB2, RC1, and RC2 should be unblocked.

The terminal 70 is connected to a counter 75. Thus, counter 75 counts books which are bad and "present". The terminal 74 can also be used to count bad books, but only when the sensors are not improperly indicating a blocked condition.

If desired, the terminals 70, 71 and/or 74 can be connected to any suitable type of monitoring circuit to provide audible and/or visual indications of bad books and improperly blocked sensors or to stop the binding line (i.e. the conveyor 10) if a "1" appears on the terminal 70 for a predetermined number of books (e.g. three consecutive books). Moreover, the monitoring circuit can also operate a reject relay as described above to reject bad books.

LED's 75 are provided in order to assist in timing adjustments and in adjustments of the sensitivity of the sensors A1–C2. The LED's 75 pulse while books are being sensed by their corresponding sensors, assuming that the sensors are functioning properly. If a sensor is permanently on or off, its associated LED is steadily on or off indicating that the detector has failed. Thus, when the terminal 71 indicates that one of the sensors is experiencing a blocked sensor failure mode, the LEDs 75 can be used to identify the specific failed sensor.

I claim:

1. A system for detecting the dimensions of a book comprising:

sensing means for sensing first and second edges of a book, said sensing means including a first sensor for sensing said first edge of said book and second and third sensors for sensing said second edge of said book, wherein said first edge is opposite to said second edge, and wherein said first, second and third sensors are spaced so that a book having predetermined dimensions covers said first and third sensors but not said second sensor; and, circuit means connected to said first, second and third sensors and responsive to said first sensor for providing a first output indicating that said book has said predetermined dimensions and a second output indicating that said book fails to have said predetermined dimensions, said first output being provided when said first and third sensors but not said second sensor are covered by said book and said second output being provided otherwise.

2. The system of claim 1 wherein said circuit means comprises means connected to said first, second and third sensors and responsive to said first sensor being covered by said book for providing said first output when said third sensor but not said second sensor is covered by said book and for providing said second output when said second and third sensors are either both covered or both uncovered by said book.

3. The system of claim 1 wherein said circuit means comprises a flip-flop having a clock input terminal, a data input terminal and an output terminal, first connecting means for connecting said clock input terminal to said first sensor, and second connecting means for connecting said data input terminal to said second and third sensors, wherein said output terminal provides said first and second outputs.

4. The system of claim 3 wherein said first connecting means comprises a multivibrator for providing a pulse to said clock input terminal in response to a first sensor signal produced by said first sensor, and said second connecting means comprises an AND gate having a first input connected to said second sensor, a second input connected to said third sensor through an inverter, and an output connected to said data input terminal.

5. The system of claim 1 wherein said first sensor senses a leading edge of said book at the top of the book and said second and third sensors sense a trailing edge of said book at said top of said book, said sensing means further comprising a fourth sensor for sensing said leading edge of said book at a bottom of said book, and fifth and sixth sensors for sensing said trailing edge of said book at said bottom of said book, wherein said first, second and third sensors are spaced so that a book having predetermined dimensions at its top covers said first and third sensors but not said second sensor, and wherein said fourth, fifth, and sixth sensors are spaced so that a book having predetermined dimensions at its bottom covers said fourth and sixth sensors but not said fifth sensor.

6. The system of claim 5 wherein said circuit means comprises first means connected to said first, second, and third sensors and responsive to said first sensor for providing said first output when said first and third sensors but not said second sensor are covered by a book and for providing said second output otherwise, and wherein said circuit means further comprises second means connected to said fourth, fifth and sixth sensors and responsive to said fourth sensor for providing a third output when said fourth and sixth sensors but not said fifth sensor are covered by a book and for providing a fourth output otherwise.

7. The system of claim 6 wherein said first means comprises a first flip-flop having a first clock input terminal, a first data input terminal and a first output terminal, first connecting means for connecting said first clock input terminal to said first sensor, and second connecting means for connecting said first data input terminal to said second and third sensors, said first output terminal for providing said first and second outputs of said first means, and wherein said second means comprises a second flip-flop having a second clock input terminal, and second data input terminal and a second output terminal, third connecting means for connecting said second clock input terminal to said fourth sensor, and fourth connecting means for connecting said second data input terminal to said fifth and sixth sensors, said second output terminal for providing said third and fourth outputs of said second means.

8. The system of claim 7 wherein said first connecting means comprises a first multivibrator for providing a pulse to said first clock input terminal in response to a signal from said first sensor, wherein said second connecting means comprises a first AND gate having a first input connected to said second sensor, a second input connected to said third sensor through an inverter, and an output connected to said first data input terminal, wherein said third connecting means comprises a second multivibrator for providing a pulse to said second clock input terminal in response to a signal from said fourth sensor, and wherein said fourth connecting means comprises a second AND gate having a first input connected to said fifth sensor, a second input connected to said sixth sensor through an inverter, and an output connected to said second data input terminal.

9. A system for detecting dimensions of a book, wherein the book has a direction of travel, the system comprising:

sensing means for sensing edges of the book, the sensing means including first and second sensors aligned with respect to one another in the direction of travel of the book;

circuit means responsive to said sensing means for detecting that the book fails to have predetermined dimensions; and, detecting means for detecting a failure of said sensing means.

10. The system of claim 9 wherein said first sensor is arranged to sense a first edge of said book and said second sensor is arranged to sense a second edge of said book, said first edge of said book being opposite to said second edge of said book.

11. The system of claim 10 wherein said detecting means comprises means for determining a failure of said first sensor by determining that said first sensor permanently senses a presence of said book and a failure of said second sensor by determining that said second sensor permanently senses a presence of said book.

12. The system of claim 11 wherein said circuit means comprises means responsive to said first and second sensors for providing a first output when said first sensor and said second sensor are in a first state with respect to one another and for providing a second output when said first sensor and said second sensor are in a second state with respect to one another.

13. The system of claim 10 wherein said sensing means further comprises a third sensor for sensing said second edge of said book, wherein said first, second and third sensors are spaced so that a book having predetermined dimensions covers said first and third sensors but not said second sensor.

14. The system of claim 13 wherein said detecting means comprises sensor failure determining means for determining a failure of said first sensor by determining that said first sensor permanently senses a presence of said book and a failure of said second and/or third sensors by determining that said second and/or sensors permanently sense a presence of said book.

15. The system of claim 14 wherein said sensor failure determining means comprises a first flip-flop having a first clock terminal, first position sensing means for providing a clock pulse to said first clock terminal while said first sensor is uncovered by said book, and first connecting means connecting a first data terminal of said first flip-flop to said first sensor, and wherein said detecting means further comprises a second flip-flop having a second clock terminal, second position sensing means for providing a clock pulse to said second clock terminal while said second and third sensors are uncovered by said book, and second connecting means connecting a second data terminal of said second flip-flop to said second and third sensors.

16. The system of claim 15 wherein said first connecting means comprises inverting means for supplying an inverted output of said first sensor to said first data terminal and said second connecting means comprises AND gate means for providing an output to said second data terminal, said AND gate means having a first input connected to said second sensor and a second input connected to said third sensor.

17. The system of claim 16 wherein said circuit means comprises means connected to said first, second and third sensors and responsive to said first sensor for providing a first output when said first and third sensors but not said second sensor are covered by a book and for providing a second output otherwise.

18. The system of claim 17 wherein said means connected to said first, second and third sensors comprises a third flip-flop having a third clock input terminal, a third data input terminal and an output terminal, third connecting means for connecting said third clock input terminal to said first sensor, and fourth connecting means for connecting said third data input terminal to said second and third sensors, and said output terminal of said third flip-flop for providing said first and second outputs.

19. The system of claim 18 wherein said third connecting means comprises a multivibrator for providing a pulse to said third clock input terminal in response to a signal from said first sensor, and wherein said fourth connecting means comprises an AND gate having a first input connected to said second sensor, a second input connected to said third sensor through an inverter, and an output connected to said third data input terminal.

20. The system of claim 13 wherein said first sensor senses a leading edge of said book at the top of the book and said second and third sensors sense a trailing edge of said book at said top of said book, said sensing means further comprising a fourth sensor for sensing said leading edge of said book at a bottom of said book, and fifth and sixth sensors for sensing said trailing edge of said book at said bottom of said book, wherein said first, second and third sensors are spaced so that a book having predetermined dimensions at its top covers said first and third sensors but not said second sensor, and wherein said fourth, fifth, and sixth sensors are spaced so that a book having predetermined dimensions at its bottom covers said fourth and sixth sensors but not said fifth sensor.

21. The system of claim 20 wherein said detecting means comprises sensor failure determining means for determining a failure of said first or fourth sensor by determining that said first or fourth sensor permanently senses a presence of said book or of said second, third, fifth, or sixth sensor by determining that said second, third, fifth, or sixth sensor permanently senses a presence of said book.

22. The system of claim 21 wherein said sensor failure determining means comprises a first flip-flop, first position sensing means for providing a clock pulse to a first clock terminal of said first flip-flop at a time when said first and fourth sensors are uncovered by said book, and first connecting means connecting a first data terminal of said first flip-flop to said first and fourth sensors, said first flip-flop having an output terminal for providing an output indicating that said first or fourth sensor is covered by said book when, in fact, said first or fourth sensor is uncovered, said sensor failure determining means further comprises a second flip-flop, second position sensing means for providing a clock pulse to a second clock terminal of said second flip-flop at a time when said second, third, fifth and sixth sensors are uncovered by said book, and second connecting means connecting a second data terminal of said second flip-flop to said second, third, fifth and sixth sensors, said second flip-flop having an output terminal for providing an output indicating that said second, third, fifth or sixth sensor is covered by said book when, in fact, said second, third, fifth and sixth sensors are uncovered.

23. The system of claim 22 wherein said first connecting means comprises first AND gate means having a first input connected to said first sensor through an inverter, a second input connected to said fourth sensor through an inverter, and an output connected to said first data terminal, and said second connecting means comprises second AND gate means having a first input connected to said second sensor, a second input connected to said third sensor, a third input connected to said fifth sensor, a fourth input connected to said sixth sensor, and an output connected to said second data terminal.

24. The system of claim 23 wherein said circuit means comprises first means connected to said first, second and third sensors and responsive to said first sensor for providing a first output when said first and third sensors but not said second sensor are covered by a book and for providing a second output otherwise, and wherein said circuit means further comprises second means connected to said fourth, fifth and sixth sensors and responsive to said fourth sensor for providing a third output when said fourth and sixth sensors but not said fifth sensor are covered by a book and for providing a fourth output otherwise.

25. The system of claim 24 wherein said first means comprises a third flip-flop having a third clock input terminal, a third data input terminal and a third output terminal, third connecting means for connecting said third clock input terminal to said first sensor, and fourth connecting means for connecting said third data input terminal to said second and third sensors, said third output terminal for providing said first and second outputs, and wherein said second means further comprises a fourth flip-flop having a fourth clock input terminal, a fourth data input terminal and a fourth output terminal, fifth connecting means for connecting said fourth clock input terminal to said fourth sensor, and sixth connecting means for connecting said fourth data input terminal to said fifth and sixth sensors, said fourth output terminal for providing said third and fourth outputs.

26. The system of claim 25 wherein said third connecting means comprises a first multivibrator for providing a pulse to said third clock input terminal in response to a signal from said first sensor, wherein said fourth connecting means comprises an AND gate having a first input connected to said second sensor, a second input connected to said third sensor through an inverter, and an output connected to said third data input terminal, wherein said fifth connecting means comprises a second multivibrator for providing a pulse to said fourth clock input terminal in response to a signal from said fourth sensor, and wherein said sixth connecting means comprises an AND gate having a first input connected to said fifth sensor, a second input connected to said sixth sensor through an inverter, and an output connected to said fourth data input terminal.

27. A system of claim 26 wherein said circuit means further comprises output means connected to said output terminals of said first, second, third and fourth flip-flops for providing an indication of a book failing to have predetermined dimensions when all of said first, second, third, fourth, fifth, and sixth sensors have not failed.

* * * * *